United States Patent [19]
Müller et al.

[11] Patent Number: 5,401,270
[45] Date of Patent: Mar. 28, 1995

[54] APPLICATOR DEVICE FOR LASER RADIATION

[75] Inventors: Gerhard Müller, Berlin; Christian Zur, Bad Saarow; Karl-Heinz Schönborn, Mainz; Jürgen Beuthan, Bad Saarow; Hubertus C. Bader, Mainz, all of Germany

[73] Assignee: Carl-Zeiss-Stiftung, Heidenheim, Germany

[21] Appl. No.: 185,023

[22] Filed: Jan. 24, 1994

Related U.S. Application Data

[62] Division of Ser. No. 810,508, Dec. 19, 1991, abandoned.

[30] Foreign Application Priority Data

Dec. 19, 1990 [DE] Germany .................. 40 41 234.2

[51] Int. Cl.⁶ ........................................... A61B 17/36
[52] U.S. Cl. .................................... 606/13; 606/15; 606/17; 606/16
[58] Field of Search ................. 606/15, 16, 17, 4, 13

[56] References Cited

U.S. PATENT DOCUMENTS

| | | | |
|---|---|---|---|
| 4,336,809 | 6/1982 | Clark | 606/15 |
| 4,560,248 | 12/1985 | Cramp et al. | 128/636 |
| 4,660,925 | 4/1987 | McCaughan, Jr. | 606/16 |
| 4,693,244 | 9/1987 | Daikuzono | 606/16 |
| 4,693,556 | 12/1987 | McCaughan, Jr. | 606/16 |
| 4,718,417 | 1/1988 | Kittrell et al. | 606/15 |
| 4,4,736,743 | 4/1988 | Daikuzono | 606/17 |
| 4,862,888 | 9/1989 | Yessik | 606/4 |

*Primary Examiner*—Stephen C. Pellegrino
*Assistant Examiner*—Sonja C. Harris
*Attorney, Agent, or Firm*—Walter Ottesen

[57] ABSTRACT

Applicator device for laser radiation wherein the end of the radiation conducting light-wave conductor faces toward the object to be treated and is mounted in a tube-like sleeve which is closed and transparent at the end for the laser radiation. The end of the sleeve and/or the end of the light-wave conductor are provided with a scattering device which includes a scattering volume. For this purpose, the application of the scattering medium can be adapted to the particular requirement.

10 Claims, 3 Drawing Sheets

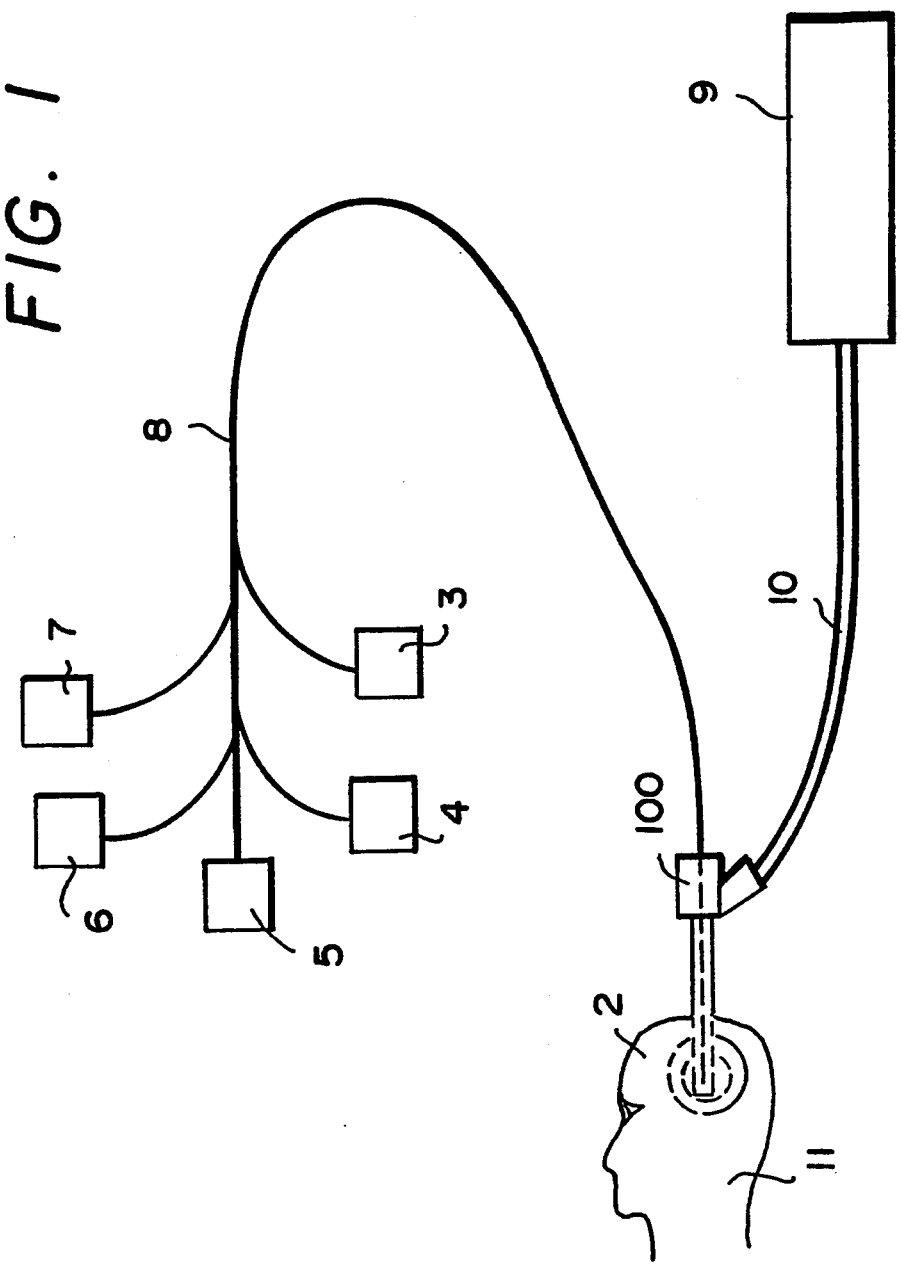

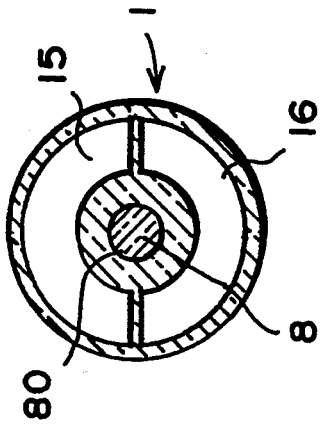
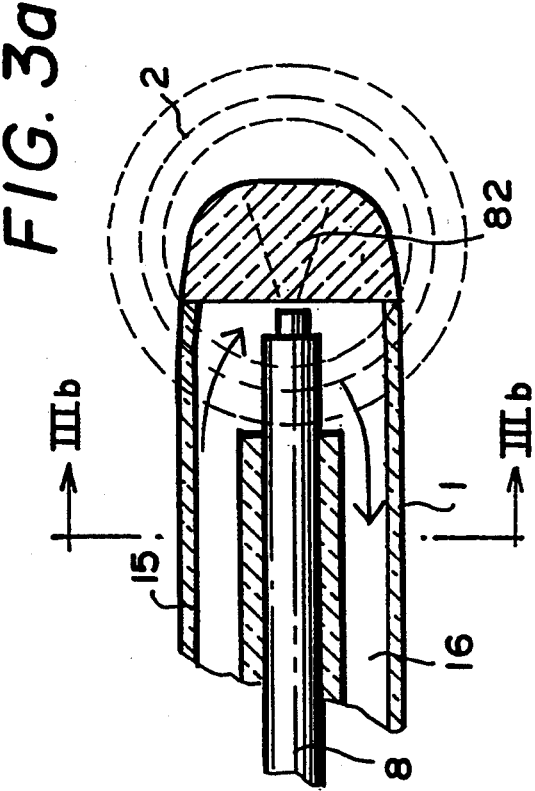
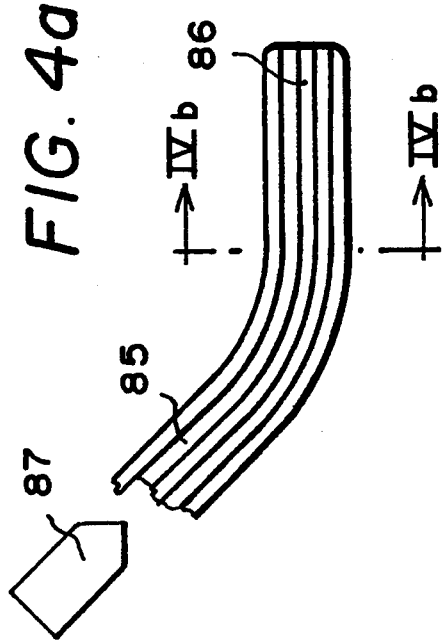

APPLICATOR DEVICE FOR LASER RADIATION

This is a division of application Ser. No. 07/810,508, filed Dec. 19, 1991, abandoned.

BACKGROUND OF THE INVENTION

It is known to produce radial-symmetrical coagulation necrosis in biological tissue with the laser radiation emanating from an optical light-wave conductor. For example, the radiation of an Nd:YAG-laser at 1.064 nm can be used with an optical fiber made of quartz glass (PCS-type, HCS-type or ALL-SILICA-type) as the radiation guiding system. For this purpose, the light-guiding fiber is either held on the tissue or inserted therein. The light distribution in the tissue takes place utilizing the inherent scattering of the particular tissue. However, the disadvantage must be accepted that a high energy density occurs at the contact location between the end surface of the fiber and the tissue. This energy density is dependent upon the fiber diameter and leads to the carbonization of the tissue surface at a light energy above a few 100 mW and, in this way, prevents a further spread of the radiation in the tissue because of the high absorption of the carbon. It is therefore necessary to realize an all-around radiation characteristic of the laser radiation at the distal end of the light conductor. For this purpose, the laser radiation exiting with limited aperture angle from the fiber must be influenced in its exiting and radiation characteristic. Accordingly, it is known to use multimode light-wave conductors for transmitting optical modes of high order (ring modes), for example, by oblique coupling in. When using a PCS-fiber, a radially symmetrical conical radiation of the laser energy is obtained after removal of the optical cladding at the distal end. At the same time, the unobstructed optical surface is protected by means of a glass tube which is attached with adhesive to the cladding on the non-decladded portion of the optical fiber. An applicator device of this kind is a commercially available product of the MBB-Medizintechnik Company with the product being known commercially as an "ITT-PROBE". Such an applicator according to the state of the art however has several disadvantages. Accordingly, the risk is present that the protective glass tube, which is only attached with adhesive, separates at the distal end and that thereby disadvantages result for the patient. On the other hand, a defined excitation of the ring mode requires an increased optical complexity at the coupling-in end.

SUMMARY OF THE INVENTION

In view of the foregoing, it is an object of the invention to provide an applicator device of the kind described above which enables higher light energies, especially those of more than 5 W, to be distributed in tissue without the danger of surface carbonization. A control of the particular radiation distribution is thereby possible.

The applicator device of the invention is for treating an object with laser radiation. The applicator device includes: a light-wave conductor for conducting the laser radiation; the light-wave conductor having an end portion directed toward the object to be treated; a tubular-shaped body disposed in surrounding and enclosing relationship to the light-wave conductor; the tubular-shaped body having a closed end portion transparent to the laser radiation and the closed end portion being adjacent to the end portion of the light-wave conductor; scattering meal is defining a volume for passing the laser radiation toward the object to be treated; and, the scattering means being arranged on one of the end portions and being substantially transparent for the laser radiation.

What is essential for the invention is that for generating radial-symmetrical coagulation necrosis in biological tissue in the region of the light conductor outlet surface, a scattering device is provided which comprises a scattering medium. The scattering medium on the one hand reduces the radiated light energy per unit of surface while, on the other land, increasing the surface to be treated. The device according to the invention is suitable for utilizing photochemical reactions in the tissue for therapeutic purposes. The device of the invention is also suitable for photodynamic therapy, that is, for generating temperature fields in order to obtain a uniform irradiation. In addition, the appropriate selection of the scattering medium permits the scattering action to be adjusted whereby the particular radiation characteristic can be dimensioned to the specific application. Such an applicator device can be economically applied to tile distal end of the light conductor.

It is preferable to provide a plastic tube which is closed in an airtight and moistureproof manner at the distal end. The distal end of this plastic tube is filled with a scattering medium in dependence upon the desired spread of the coagulation necrosis to be produced. The medium does not absorb at the effective wavelength or absorbs only minimally. Such an applicator device affords the advantage in manufacture that conventional individual fiber applicators can be introduced into the plastic tube until the fiber end finally reaches the particular scattering medium.

Also, high laser energies can be radiated uniformly radially in dependence upon the scattering distance adjustable by the selection of the scattering medium. Only low primary energy densities result at the surface of the plastic tube so that carbonization of the tissue in contact therewith can be reliably prevented.

A possibility for the selection of a scattering medium is provided in the use of a glass body which contains pores or crystallite as scattering centers. Such porous glass material is also known under the name of "foam glass" or "open-pore sinter glass". The pore volume portion and/or the mean pore size can be definitively adjusted in the production of this kind of material. For this reason, the desired scattering effect can be controlled. The same applies to the magnitude or volume portion of the crystallite. It has been shown advantageous to configure the scattering device from this material as a capillary. Alternatively, the form of a cylinder, sphere or cone is also possible.

According to another embodiment of the invention, the plastic tube is made of Teflon (PTFE) and the scattering medium comprises a Teflon plug which simultaneously functions as a distal closure of the tube. PTFE material filled with barium sulfate or titan (IV) oxide can be used to increase the scattering capacity. However, he application is not limited to Teflon but any biocompatible plastic material can be used which is non-absorbent at the effective wavelength range of the laser used.

According to another embodiment of the invention, multiple-chambered tubes can be used to carry out an additional rinsing and cooling of the fiber end. In this case, branching pieces and sealing devices for introducing the fiber are provided at the proximal end of the encasing tube.

In still another embodiment of the invention, an encasing tube closed at the distal end is used and the fiber end is itself freed from the optical cladding and matted so that a radially-symmetrical radiation is obtained from the optical roughening.

Likewise, an encasing sleeve of this kind can also be utilized in combination with the known ring mode applicator of the MBB-Medizintechnik Company in order to reliably prevent a separation of the distal glass tube. The length of the encasing sleeve is dimensioned while considering the particular area of use and leads to various embodiment sizes of the device of the invention ill accordance with indications provided from clinical use.

A mechanically stiff trocar (as a rule, a metallic cannula) is used to introduce the thin-walled encasing tube in the center of the tissue area to be irradiated with this being done in dependence upon the firmness of the tissue. The encasing sleeve is guided through the trocar and the trocar is withdrawn after successful introduction in order to clear the location to be irradiated. Configurations are also possible wherein the metal trocar is completely removed before the application of the laser radiation. This is especially of significance when the application is under NMR-control when no metal parts can be tolerated in high magnetic fields.

In the event that the tissue is relatively soft, a mechanically stiff mandrin can be used in lieu of the mechanically stiff trocar in order to place the applicator. Thereafter, the mechanically stiff mandrin is removed and the light-conducting fiber is introduced in lieu thereof.

A typical application of such an applicator device is the interstitial laser coagulation of tumors under X-ray or NMR-control. Enriching the scattering medium with barium sulfate has been shown to be advantageous especially for the X-ray control of the placement because a good X-ray contrast is obtained therewith. In contrast, with NMR-control a suitable magnetically-active marker medium can be introduced into the encasing body for the light-wave conductor and/or into the scatter medium.

According to another embodiment, the laser radiation is coupled into several parallelly directed light-wave conductors which are tightly connected with each other at the distal end. In this way, the condition is obtained that the scattering device is uniformly charged with laser radiation. The scattering device, in turn, is a fixed component of the fiber end or is mounted in the encasing tube. In addition, several lasers can be utilized at the same time for therapy.

BRIEF DESCRIPTION OF THE DRAWINGS

The invention will now be described with reference to the drawings wherein:

FIG. 1 is a schematic showing the application of the device according to the invention;

FIG. 3a is a side elevation view, in section, of a multi-luminous embodiment of the applicator;

FIG. 3b is a section view taken along line IIIb—IIIb of FIG. 3a;

FIG. 4a shows an applicator device according to another embodiment of the invention with a multi-fiber light-wave conductor; and, FIG. 4b is a section view taken along line IVb-IVb of FIG. 4a.

Figure 2A:
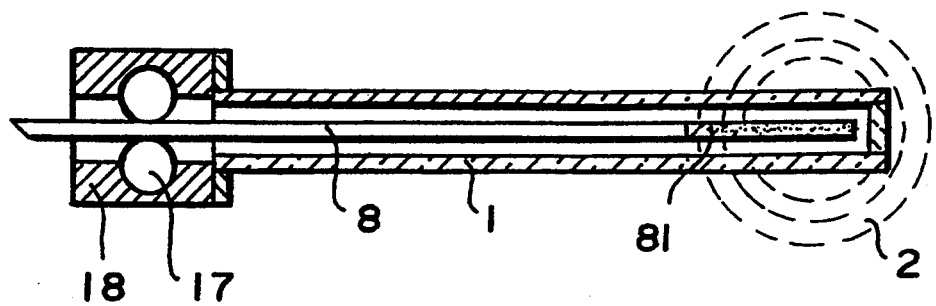
FIG. 2a is a detail of the scattering device shown in the device of FIG. 1 and having a single light-wave conductor.

DESCRIPTION OF THE PREFERRED
EMBODIMENTS OF THE INVENTION

FIG. 1 is a schematic silowing an embodiment of the applicator device according to the invention for treating a brain tumor on a patient 11. The scattering volume obtainable therewith and the tissue volume which can be treated is shown schematically with the partial circles 2. The end of the light-wave conductor 8 can simultaneously be rinsed and cooled by means of the rinsing device 9 and a rinsing channel 10 during the therapy. The light-wave conductor 8 comprises one or several individual fibers into which several lasers (3 to 7) are coupled. The laser radiation used can lie in the spectral range between 400 and 3000 nm in accordance with the specific application.

FIG. 2a shows a detail view of the applicator device 100 of FIG. 1 according to another embodiment with only a single light-wave conductor 8. This light-wave conductor is roughened at its distal end in region 81 in order to realize the desired scattering effect. The light-wave conductor used is roughened at its end face as well as in a cylindrical region 81 of its surface lying at the end face. The light-wave conductor 8 can, without limitation, be utilized in the conventional applicator devices. In the embodiment shown, a seal of the light-wave conductor 8 within the sleeve 1 is provided for a suction-rinsing device 17. The seal has a standard luer lock 18.

Figure 2B:
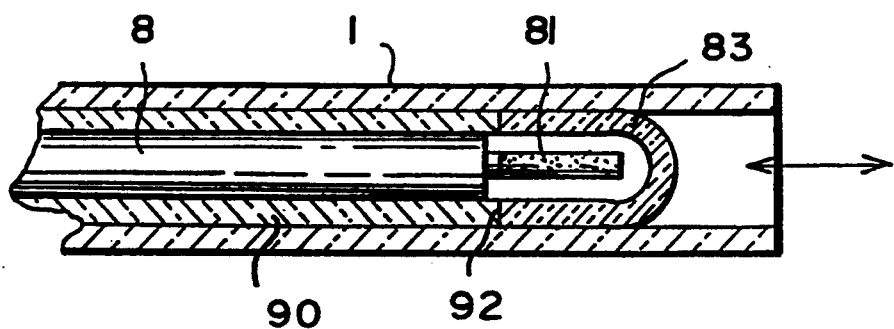
FIG. 2b is a configuration of the scattering device for increasing the scattering efficiency with a second matted sleeve cap.

In the embodiment shown in FIG. 2b, an additional matted sleeve cap 83 is provided for increasing the scattering efficiency; more specifically, a scattering capillary is pushed over the end 81 of the light-wave conductor 8 and abuts against inner sleeve 90 holding the light-wave conductor. This sleeve cap makes a sliding guidance possible within the sleeve 1 forming the guide body because of the cross-sectional enlargement in the end region obtained thereby. The light-wave conductor 8, inner sleeve 90 and sleeve cap 83 are displaced as a unit within sleeve 1 and displacement takes place in the direction of the arrow. The sleeve cap 83 can be joined to the inner sleeve at abutting interface 92 by a suitable joining means such as an adhesive.

Figure 2C:
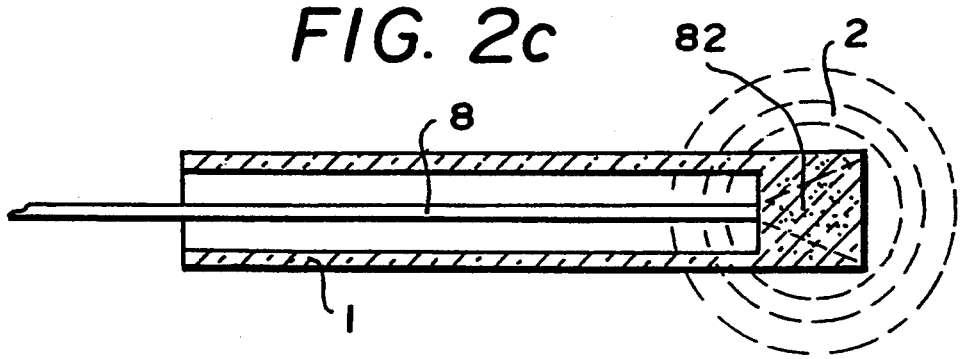
FIG. 2c is a configuration of the scattering device mounted in an outer sleeve body.

In FIG. 2c, an applicator device is shown wherein a scattering device in the form of a scattering volume body 82 is mounted in the outer sleeve 1 at the end thereof. The light-wave conductor 8 borders oil this scattering volume body 82 at the end of the sleeve 1 and an irradiation of the region 2 results. The scattering volume body 82 can comprise PTFE filled with barium sulfate or titan (IV) oxide and simultaneously forms a hermetic seal for the distal end of the sleeve 1. Likewise, the scatter volume body 82 can also be made of another material which satisfies the corresponding requirements. The so-called "foam glass" or "open-pore sinter glass" which contain pores or crystallite are for example suitable. By adjusting the volume portion and/or the mean magnitude of the scattering centers during the manufacture of the particular material, the radiation characteristic can be varied to be specific for the application. The high temperature resistance as well as the resistance with respect to the laser radiation used can be advantageous with a porous glass material.

Figure 2D:
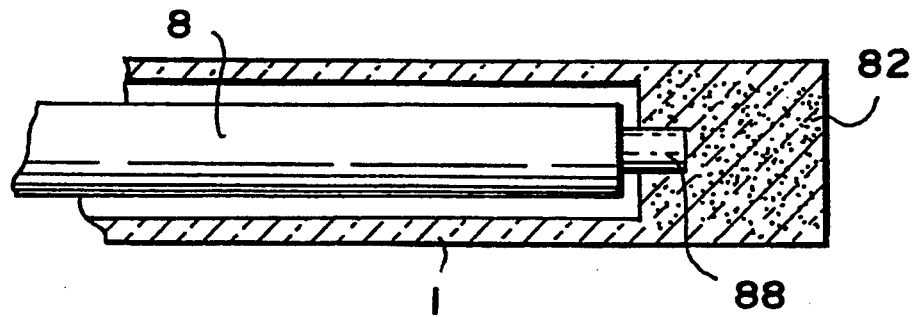
FIG. 2d is another embodiment of the applicator device of the invention wherein the light-wave conductor extends into the scatter volume body.

FIG. 2d shows another embodiment of the invention wherein additionally the end of the core 88 of the light-wave conductor 8 is introduced into the scatter volume body 82 to prevent reflections. The scatter volume body 82 includes a cutout which is adapted to the outer dimensions of the end of the light-wave conductor 8 so that a stable mechanical fixation between the end of the light-wave conductor and the scatter volume body 82 is achieved.

Different geometries have been described for the respective scattering devices shown in FIGS. 2a to 2d. In addition to these embodiments, many other possibilities exist to arrange the light-wave conductor and the scattering device relative to each other. Accordingly, it is possible to manufacture the scatter volume body in the form of a cylinder, a sphere or a cone into which the end of the light-wave conductor extends.

The connection between the end of the light-wave conductor and the scatter volume body can be achieved by means of a suitable adhesive as well as by direct melting for example with a laser.

It is also advantageous to provide the complete device at the end of the light-wave conductor and to provide capillaries with a protective jacket by means of which tile particular components and the patient are protected. This protective jacket must be transparent for the laser radiation used as well as be seal-tight at the distal end.

In FIG. 3a, a sleeve having several individual channels is shown in a side elevation view wherein the inner channel 80 is provided for introducing the light-wave conductor and the outer component channels 15 and 16 are provided for rinsing and drawing off by suction. The rinsing channels are so configured that the rinsing medium forms a part of the scattering device and/or cleans the surface of the light-wave conductor and the scattering volume body 82, that is, frees tile latter from adhering particles aid the like which, for example, separate from the material of the light-wave conductor 8 and/or sleeve 1 because of heat developed during radiation.

FIG. 3b shows a section of the embodiment of FIG. 3a.

FIG. 4a is a side elevation view of an applicator device wherein several parallel light-wave conductors are provided for homogenizing the laser radiation and for obtaining a higher scattering efficiency. The ends of the individual fibers 85 of the multi-fiber light-wave conductor are tightly connected with each other in a specific region 86. The laser 87 used is here configured as either a diode laser or semiconductor laser. The end region of the multi-fiber light-wave conductor device is bounded by a scattering device which was described with the embodiments shown in the other figures. The light distribution is especially homogenized with the aid of this device.

The section taken through region 86 is shown in FIG. 4b.

The invention is not limited to the embodiments described above but rather a number of variations are conceivable which are based on the principle described.

It is understood that the foregoing description is that of the preferred embodiments of the invention and that various changes and modifications may be made thereto without departing from the spirit and scope of the invention as defined in the appended claims.

What is claimed is:

1. An applicator device for interstitially treating biological tissue with laser radiation in the spectral range of 400 to 3000 nm to produce radial-symmetrical coagulation necrosis in the biological tissue, the applicator device comprising:

a light-wave conductor for conducting the laser radiation;

said light-wave conductor being configured as an optical fiber and having an exposed end portion directed toward the biological tissue to be treated;

a tubular-shaped body disposed in surrounding and enclosing relationship to said light-wave conductor;

said tubular-shaped body having a closed end portion transparent to said laser radiation and said closed end portion being adjacent to said end portion of said light-wave conductor;

scattering means for homogenizing and passing laser radiation intensity toward the biological tissue to be treated;

said scattering means being arranged on said end portion of said light-wave conductor and being substantially transparent for said laser radiation;

said closed end portion of said tubular-shaped body being air tight and impermeable to a liquid;

said end portion of said light-wave conductor being roughened to define said scattering means; and, said exposed end portion of said light-wave conductor and said closed end portion of said tubular-shaped body conjointly defining a gap therebetween.

2. The applicator device of claim 1, said light-wave conductor defining a longitudinal axis and said scattering means being configured so as to be multilayered and symmetrical with respect to said axis.

3. The applicator device of claim 1, said scattering means further comprising said closed end portion of said tubular-shaped body configured as a scattering capillary.

4. The applicator device of claim 1, said tubular-shaped body defining a longitudinal axis and said applicator device further comprising: holding means for holding said tubular-shaped body and said light-wave conductor so as to permit said tubular-shaped body and said light-wave conductor to be displaceable as a unit in said holding means along said axis.

5. The applicator device of claim 4, said holding means comprising a sleeve having an open outer end; and, said closed end portion of said tubular-shaped body being a cap having a tapered forward end to facilitate movement of said unit in said sleeve along said longitudinal axis.

6. The applicator device of claim 5, said scattering means including said cap configured as a matted cap pushed over said end portion of said light-wave conductor.

7. The applicator device of claim 1, said tubular-shaped body being made of polytetrafluorethylene.

8. The applicator device of claim 1, said tubular-shaped body being made of polyethylene.

9. The applicator device of claim 1, said scattering means being configured as a scattering body having a geometric form.

10. The applicator device of claim 1, further comprising protective jacket means for protecting said light-wave conductor and said scattering means.

* * * * *

UNITED STATES PATENT AND TRADEMARK OFFICE
CERTIFICATE OF CORRECTION

PATENT NO. : 5,401,270                 Page 1 of 2

DATED : March 28, 1995

INVENTOR(S) : Gerhard Müller, Christian Zur, Karl-Heinz Schönborn, Jürgen Beuthan and Hubertus C. Bader.

It is certified that error appears in the above-identified patent and that said Letters Patent is hereby corrected as shown below:

On the title page, under "U.S. PATENT DOCUMENTS", item [56], line 3: delete "606/16" and substitute -- 606/15 -- therefor.

On the title page, under "U.S. PATENT DOCUMENTS", item [56], line 7: delete "4,4,736,743" and substitute -- 4,736,743 -- therefor.

In column 2, line 2: delete "meal is" and substitute -- means -- therefor.

In column 2, line 13: delete "land" and substitute -- hand -- therefor.

In column 2, line 24: delete "tile" and substitute -- the -- therefor.

In column 2, line 62: delete "he" and substitute -- the -- therefor.

In column 3, line 15: delete "ill" and substitute -- in -- therefor.

In column 4, line 16: delete "silowing" and substitute -- showing -- therefor.

In column 4, line 59: delete "oil" and substitute -- on -- therefor.

UNITED STATES PATENT AND TRADEMARK OFFICE
CERTIFICATE OF CORRECTION

PATENT NO. : 5,401,270

DATED : March 28, 1995

INVENTOR(S) : Gerhard Müller, Christian Zur, Karl-Heinz Schönborn, Jürgen Beuthan and Hubertus C. Bader.

It is certified that error appears in the above-identified patent and that said Letters Patent is hereby corrected as shown below:

In column 5, line 31:  delete "tile" and substitute -- the -- therefor.

In column 5, line 42:  delete "tile" and substitute -- the -- therefor.

In column 5, line 43:  delete "aid" and substitute -- and -- therefor.

Signed and Sealed this

Twenty-seventh Day of June, 1995

Attest:

BRUCE LEHMAN

Attesting Officer    Commissioner of Patents and Trademarks